US009060925B2

(12) United States Patent
Perricone et al.

(10) Patent No.: US 9,060,925 B2
(45) Date of Patent: *Jun. 23, 2015

(54) METHODS OF DELIVERING STABLE TOPICAL DRUG COMPOSITIONS

(71) Applicant: Transdermal Biotechnology, Inc., Meriden, CT (US)

(72) Inventors: Nicholas V. Perricone, Madison, CT (US); Chim Potini, Bloomington, IL (US)

(73) Assignee: Transdermal Biotechnology, Inc., Meriden, CT (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/947,329

(22) Filed: Jul. 22, 2013

(65) Prior Publication Data

US 2013/0331318 A1  Dec. 12, 2013

Related U.S. Application Data

(60) Continuation of application No. 13/019,101, filed on Feb. 1, 2011, now abandoned, which is a continuation-in-part of application No. 11/334,206, filed on Jan. 18, 2006, now abandoned, which is a division of application No. 10/448,632, filed on May 30, 2003, now abandoned, said application No. 13/019,101 is a continuation of application No. 11/344,442, filed on Jan. 31, 2006, now abandoned, which is a division of application No. 10/749,914, filed on Dec. 31, 2003, now Pat. No. 7,182,956, and a continuation-in-part of application No. 10/448,632, filed on May 30, 2003, now abandoned.

(51) Int. Cl.
| | |
|---|---|
| *A61J 3/07* | (2006.01) |
| *A61K 31/56* | (2006.01) |
| *A61K 38/02* | (2006.01) |
| *A61K 9/02* | (2006.01) |
| *A61K 9/127* | (2006.01) |
| *A61K 38/23* | (2006.01) |
| *A61K 38/28* | (2006.01) |
| *A61K 47/10* | (2006.01) |
| *A61K 47/24* | (2006.01) |
| *A61K 9/00* | (2006.01) |
| *A61K 38/27* | (2006.01) |
| *A61K 9/06* | (2006.01) |
| *A61K 38/11* | (2006.01) |
| *A61K 38/24* | (2006.01) |
| *A61K 38/31* | (2006.01) |
| *A61K 38/56* | (2006.01) |
| *A61K 47/14* | (2006.01) |
| *A61K 47/22* | (2006.01) |
| *A61K 47/34* | (2006.01) |

(52) U.S. Cl.
CPC ............... *A61K 9/0014* (2013.01); *A61K 9/127* (2013.01); *A61K 9/1277* (2013.01); *A61K 38/27* (2013.01); *A61K 38/28* (2013.01); *A61K 47/24* (2013.01); *A61K 47/10* (2013.01); *A61K 9/02* (2013.01); *A61K 9/06* (2013.01); *A61K 31/56* (2013.01); *Y10S 514/866* (2013.01); *Y10S 514/808* (2013.01); *Y10S 514/97* (2013.01); *Y10S 514/807* (2013.01); *Y10S 514/806* (2013.01); *A61K 38/02* (2013.01); *A61K 38/11* (2013.01); *A61K 38/23* (2013.01); *A61K 38/24* (2013.01); *A61K 38/31* (2013.01); *A61J 3/07* (2013.01); *A61K 38/56* (2013.01); *A61K 47/14* (2013.01); *A61K 47/22* (2013.01); *A61K 47/34* (2013.01)

(58) Field of Classification Search
CPC ........... A61J 3/07; A61K 31/56; A61K 38/02; A61K 38/11; A61K 38/23; A61K 38/24; A61K 38/27; A61K 38/28; A61K 38/31; A61K 47/10; A61K 47/24; A61K 9/0014; A61K 9/02; A61K 9/06; A61K 9/127
See application file for complete search history.

(56) References Cited

U.S. PATENT DOCUMENTS

| | | | |
|---|---|---|---|
| 4,174,296 | A | 11/1979 | Kass |
| 4,333,927 | A | 6/1982 | Ofuchi et al. |
| 4,614,730 | A | 9/1986 | Hansen et al. |
| 4,624,665 | A | 11/1986 | Nuwayser |
| 4,687,661 | A | 8/1987 | Kikuchi et al. |
| 4,708,861 | A | 11/1987 | Popescu et al. |
| 4,743,449 | A | 5/1988 | Yoshida et al. |
| 5,120,561 | A | 6/1992 | Silva et al. |
| 5,151,272 | A | 9/1992 | Engstrom et al. |
| 5,153,000 | A | 10/1992 | Chikawa et al. |

(Continued)

FOREIGN PATENT DOCUMENTS

| | | |
|---|---|---|
| CA | 2182390 A1 | 8/1995 |
| CA | 2181390 A1 | 1/1997 |

(Continued)

OTHER PUBLICATIONS

International Report on Patentability for Application No. PCT/US2012/000151 mailed Sep. 26, 2013.

(Continued)

*Primary Examiner* — Ernst V Arnold
(74) *Attorney, Agent, or Firm* — Wolf, Greenfield & Sacks, P.C.

(57) ABSTRACT

A method of delivering a drug composition comprises providing a carrier having a phosphatidylcholine component and a drug entrapped therein, and applying the composition to the skin for transdermal delivery of the drug, wherein the composition is stable at room temperature.

8 Claims, No Drawings

(56) References Cited

U.S. PATENT DOCUMENTS

| | | |
|---|---|---|
| 5,206,219 A | 4/1993 | Desai |
| 5,254,348 A | 10/1993 | Hoffmann et al. |
| 5,308,625 A | 5/1994 | Wong et al. |
| 5,380,761 A | 1/1995 | Szabo et al. |
| 5,391,548 A | 2/1995 | Francoeur et al. |
| 5,439,967 A | 8/1995 | Mathur |
| 5,476,651 A | 12/1995 | Meybeck et al. |
| 5,484,816 A | 1/1996 | Yanagida et al. |
| 5,504,117 A | 4/1996 | Gorfine |
| 5,550,263 A | 8/1996 | Herslof et al. |
| 5,576,016 A | 11/1996 | Amselem et al. |
| 5,656,286 A | 8/1997 | Miranda et al. |
| 5,662,932 A | 9/1997 | Amselem et al. |
| 5,674,912 A | 10/1997 | Martin |
| 5,693,676 A | 12/1997 | Gorfine |
| 5,726,164 A | 3/1998 | Weder et al. |
| 5,753,259 A | 5/1998 | Engstrom et al. |
| 5,776,494 A | 7/1998 | Guskey et al. |
| 5,807,573 A | 9/1998 | Ljusberg-Wahren et al. |
| 5,814,666 A | 9/1998 | Green et al. |
| 5,853,755 A | 12/1998 | Foldvari |
| 5,858,398 A | 1/1999 | Cho |
| 5,869,539 A | 2/1999 | Garfield et al. |
| 5,874,479 A | 2/1999 | Martin |
| 5,879,690 A | 3/1999 | Perricone |
| 5,891,472 A | 4/1999 | Russell |
| 5,955,502 A | 9/1999 | Hansen et al. |
| 5,976,562 A | 11/1999 | Krall et al. |
| 5,985,298 A | 11/1999 | Brieva et al. |
| 6,022,561 A | 2/2000 | Carlsson et al. |
| 6,045,827 A | 4/2000 | Russell |
| 6,103,275 A | 8/2000 | Seitz et al. |
| 6,133,320 A | 10/2000 | Yallampalli et al. |
| 6,165,500 A | 12/2000 | Cevc |
| 6,191,121 B1 | 2/2001 | Perricone |
| 6,193,997 B1 | 2/2001 | Modi |
| 6,207,713 B1 | 3/2001 | Fossel |
| 6,211,250 B1 | 4/2001 | Tomlinson et al. |
| 6,214,375 B1 | 4/2001 | Modi |
| 6,242,099 B1 | 6/2001 | Grandmontagne et al. |
| 6,287,601 B1 | 9/2001 | Russell |
| 6,294,192 B1 | 9/2001 | Patel et al. |
| 6,391,869 B1 | 5/2002 | Parks et al. |
| 6,458,841 B2 | 10/2002 | Fossel |
| 6,464,987 B1 | 10/2002 | Fanara et al. |
| 6,521,250 B2 | 2/2003 | Meconi et al. |
| 6,538,061 B2 | 3/2003 | Chaiyawat et al. |
| 6,555,573 B2 | 4/2003 | Rosenbloom |
| 6,780,849 B2 | 8/2004 | Herrmann et al. |
| 6,932,963 B2 | 8/2005 | Perricone |
| 6,936,044 B2 | 8/2005 | McDaniel |
| 7,033,574 B1 | 4/2006 | Schneider et al. |
| 7,182,956 B2 | 2/2007 | Perricone et al. |
| 7,189,761 B2 | 3/2007 | Gorfine |
| 7,696,247 B2 | 4/2010 | Herrmann et al. |
| 7,820,420 B2 | 10/2010 | Whitlock |
| 7,976,743 B2 | 7/2011 | Huang et al. |
| 8,273,711 B2 | 9/2012 | Perricone |
| 8,435,942 B2 | 5/2013 | Perricone et al. |
| 8,668,937 B2 | 3/2014 | Perricone et al. |
| 8,871,254 B2 | 10/2014 | Perricone |
| 8,871,255 B2 | 10/2014 | Perricone |
| 8,871,256 B2 | 10/2014 | Perricone |
| 8,871,257 B2 | 10/2014 | Perricone |
| 8,871,258 B2 | 10/2014 | Perricone |
| 8,871,259 B2 | 10/2014 | Perricone |
| 8,871,260 B2 | 10/2014 | Perricone |
| 8,871,261 B2 | 10/2014 | Perricone |
| 8,871,262 B2 | 10/2014 | Perricone |
| 2002/0131994 A1 | 9/2002 | Schur et al. |
| 2002/0153509 A1 | 10/2002 | Lynch et al. |
| 2002/0160040 A1 | 10/2002 | Spicer et al. |
| 2002/0182162 A1 | 12/2002 | Shahinpoor et al. |
| 2004/0018237 A1 | 1/2004 | Perricone |
| 2004/0096494 A1 | 5/2004 | Siekmann et al. |
| 2004/0191305 A1 | 9/2004 | Perricone et al. |
| 2004/0197391 A1 | 10/2004 | Perricone et al. |
| 2005/0226945 A1 | 10/2005 | Ruwart |
| 2006/0105955 A1 | 5/2006 | Perricone |
| 2006/0127469 A1 | 6/2006 | Perricone et al. |
| 2006/0275353 A1 | 12/2006 | Perricone et al. |
| 2009/0214624 A1 | 8/2009 | Smith et al. |
| 2009/0304815 A1 | 12/2009 | Cossu et al. |
| 2009/0324698 A1 | 12/2009 | Wagner et al. |
| 2010/0048520 A1 | 2/2010 | Safdi et al. |
| 2010/0292139 A1 | 11/2010 | Perricone |
| 2010/0311696 A1 | 12/2010 | Perricone |
| 2011/0104240 A1 | 5/2011 | Jones et al. |
| 2011/0123577 A1 | 5/2011 | Perricone et al. |
| 2012/0156163 A1 | 6/2012 | Bauman et al. |
| 2013/0029989 A1 | 1/2013 | Coderre et al. |
| 2013/0059017 A1 | 3/2013 | Perricone et al. |
| 2013/0330380 A1 | 12/2013 | Perricone |
| 2013/0330381 A1 | 12/2013 | Perricone et al. |
| 2013/0331319 A1 | 12/2013 | Perricone et al. |
| 2014/0271730 A1 | 9/2014 | Perricone |
| 2014/0271731 A1 | 9/2014 | Perricone |
| 2014/0271732 A1 | 9/2014 | Perricone |
| 2014/0271742 A1 | 9/2014 | Perricone |
| 2014/0271743 A1 | 9/2014 | Perricone |
| 2014/0271800 A1 | 9/2014 | Perricone |
| 2014/0271801 A1 | 9/2014 | Perricone |
| 2014/0271802 A1 | 9/2014 | Perricone |
| 2014/0271803 A1 | 9/2014 | Perricone |
| 2014/0271804 A1 | 9/2014 | Perricone |
| 2014/0271805 A1 | 9/2014 | Perricone |
| 2014/0271806 A1 | 9/2014 | Perricone |
| 2014/0271807 A1 | 9/2014 | Perricone |
| 2014/0271808 A1 | 9/2014 | Perricone |
| 2014/0271809 A1 | 9/2014 | Perricone |
| 2014/0271810 A1 | 9/2014 | Perricone |
| 2014/0271811 A1 | 9/2014 | Perricone |
| 2014/0271934 A1 | 9/2014 | Perricone |
| 2014/0271935 A1 | 9/2014 | Perricone |
| 2014/0271936 A1 | 9/2014 | Perricone |
| 2014/0271937 A1 | 9/2014 | Perricone |
| 2014/0271938 A1 | 9/2014 | Perricone |
| 2015/0004196 A1 | 1/2015 | Perricone |
| 2015/0010521 A1 | 1/2015 | Perricone |
| 2015/0010655 A1 | 1/2015 | Perricone |
| 2015/0010656 A1 | 1/2015 | Perricone |
| 2015/0010657 A1 | 1/2015 | Perricone |
| 2015/0010658 A1 | 1/2015 | Perricone |
| 2015/0010659 A1 | 1/2015 | Perricone |
| 2015/0010660 A1 | 1/2015 | Perricone |
| 2015/0010661 A1 | 1/2015 | Perricone |
| 2015/0010662 A1 | 1/2015 | Perricone |

FOREIGN PATENT DOCUMENTS

| | | |
|---|---|---|
| EP | 0482554 A2 | 4/1992 |
| EP | 0561330 A1 | 9/1993 |
| EP | 0722323 A1 | 7/1996 |
| EP | 0727323 A1 | 8/1996 |
| JP | 60-58915 A | 4/1985 |
| JP | 60-155109 A | 8/1985 |
| JP | S63-502117 A | 8/1988 |
| JP | H05-502042 A | 4/1993 |
| JP | H05-51338 B2 | 8/1993 |
| JP | H06-316530 | 11/1994 |
| JP | 10-194994 A | 7/1998 |
| JP | 11-079975 | 3/1999 |
| JP | 2000-086501 | 3/2000 |
| JP | 2000-504033 A | 4/2000 |
| JP | 2001-500886 A | 1/2001 |
| JP | 2001-507689 A | 6/2001 |
| WO | WO 87/04592 A1 | 8/1987 |
| WO | WO 92/03122 A1 | 3/1992 |
| WO | WO 98/13025 A1 | 4/1998 |
| WO | WO 98/22090 A1 | 5/1998 |
| WO | WO 99/56725 A1 | 11/1999 |
| WO | WO 01/01963 A1 | 1/2001 |
| WO | WO 01/49268 A1 | 7/2001 |
| WO | WO 01/76537 A1 | 10/2001 |

(56) References Cited

FOREIGN PATENT DOCUMENTS

| WO | WO 02/064115 A1 | 8/2002 |
|---|---|---|
| WO | WO 02/064166 A1 | 8/2002 |
| WO | WO 03/101480 A1 | 12/2003 |
| WO | WO 2004/060314 A2 | 7/2004 |
| WO | WO 2004/060315 A2 | 7/2004 |

OTHER PUBLICATIONS

Office Action mailed Aug. 26, 2013 for U.S. Appl. No. 11/506,137.
Office Action mailed Aug. 26, 2013 for U.S. Appl. No. 13/019,101.
[No Author Listed] Phosal 50 PG MSDA. 2007. 3 pages.
Agarwal et al., Preparation and In Vitro Evaluation of Miconazole Nitrate-Loaded Topical Liposomes. Pharmaceutical Technology. Nov. 2002, p. 48-60.
Barenholz et al., Handbook of nonmedical applications of liposomes. 1996;3:217.
Benson et al, "Optimization of Drug Delivery 4. Transdermal Drug Delivery," Aus J Hosp Pharm, 27(6): 441-448 (1997).
Bhattacharjee, "More Than the Patch: New Ways to Take Medicine Via Skin," New York Times, Jul. 2, 2002, p. F5.
Brannon-Peppas, Polymers in Controlled Drug Delivery. Medical Plastics and Biomaterials Magazine. Nov. 1997:34-44.
Cevc, Transdermal Drug Carriers: Basic Properties, Optimization and Transfer Efficiency in the Case of Epicutaneously Applied Peptides, Journal of Controlled Release 36: 3-16 (1995).
Chapman, Phase transitions and fluidity characteristics of lipids and cell membranes. Q Rev Biophys. May 1975;8(2):185-235.
Chetty et al., Novel Methods of Insulin Delivery: An Update, Critical Reviews in Therapeutic Drug Carrier Systems, 15(6): 629-670 (1998).
Christie, Phosphatidylcholine and Related Lipids, www.lipid.co.uk, May 5, 2003.
Cox, Roundup's inert surfactant is poisonous. Journal of Pesticide Reform. 1988 Spring;8(1):30.
Daddona, Recent Advances in Peptide, Protein and Macromolecule Drug Delivery, Current Opinion in Drug Discovery & Development, 2(2): 168-171 (1999).
Daniels, "Galenic Principles of Modern Skin Care Products," Skin Care Forum, Issue 25, Apr. 2001.
King et al., Transdermal delivery of insulin from a novel biphasic lipid system in diabetic rats. Diabetes Technol Ther. 2002;4(4):479-88.
Maurer et al., Developments in liposomal drug delivery systems. Expert Opin Biol Ther. Nov. 2001;1(6):923-47.
Mitragotri, "Synergistic Effect of Enhancers for Transdermal Drug Delivery," Pharmaceutical Research, 17(11):1354-1359 (2000).
Patki et al., "Progress Made in Non-Invasive Insulin Delivery," Indian Journal of Pharmacology, 28:143-151 (1996).
Robin, A physiological handbook for teachers of yogasana. 2002:283-5.
Trehan et al., "Recent Approaches in Insulin Delivery," Drug Development and Industrial Pharmacy, 24(7): 589-97 (1998).
Weiner et al. "Liposome-Collagen Gel Matrix: A Novel Sustained Drug Delivery System." J. Pharm. Sci. 1985, 74(9), 922-5.
International Search Report and Written Opinion for Application No. PCT/US2012/000151 mailed Aug. 20, 2012.
Examiner's Report for Application No. AU 2003303517 mailed Dec. 1, 2006.
Canadian Office Action for Application No. CA 02511849 mailed May 8, 2009.
Canadian Office Action for Application No. CA 02511849 mailed Feb. 8, 2011.
Canadian Office Action for Application No. CA 02511849 mailed Sep. 14, 2011.
Chinese Office Action for Application No. CN 200380108020.0 mailed Jan. 19, 2007.
Chinese Office Action for Application No. CN 200380108020.0 mailed Aug. 3, 2007.
Chinese Office Action for Application No. CN 200380108020.0 mailed Mar. 14, 2008.
Chinese Office Action for Application No. CN 200380108020.0 mailed Nov. 28, 2008.
Chinese Office Action for Application No. CN 200380108020.0 mailed Mar. 6, 2009.
European Communication for Application No. EP 03815011.6 mailed Aug. 11, 2005.
Supplementary European Search Report for Application No. EP 03815011.6 mailed Aug. 16, 2006.
European Communication for Application No. EP 03815011.6 mailed Dec. 15, 2008.
Summons to Attend Oral Proceedings for Application No. EP 03815011.6 mailed Mar. 31, 2010.
Israeli Office Action for Application No. IL 169169 mailed May 6, 2009.
Japanese Office Action for Application No. JP 2004-565850 mailed Mar. 24, 2009.
Japanese Office Action for Application No. JP 2004-565850 mailed Nov. 4, 2009.
Japanese Office Action for Application No. JP 2004-565850 mailed Aug. 2, 2011.
Japanese Office Action for Application No. JP 2004-565850 mailed Aug. 21, 2012.
Japanese Office Action for Application No. JP 2004-565850 mailed Mar. 5, 2013.
Korean Office Action for Application No. KR 10-2005-7012203 mailed Sep. 27, 2006.
Korean Office Action for Application No. KR 10-2005-7012203 mailed Jan. 25, 2007.
Korean Office Action for Application No. KR 10-2005-7012203 mailed Jun. 4, 2007.
Summary of Office Action issued in 2008 for MX PA/a/2005/007023.
International Search Report for Application No. PCT/US2003/041671 mailed Aug. 5, 2004.
Written Opinion for Application No. PCT/US2003/041671 mailed Oct. 21, 2004.
International Preliminary Report on Patentability for Application No. PCT/US2003/041671 completed Jan. 4, 2005.
Canadian Office Action for Application No. CA 2487305 mailed Nov. 5, 2008.
Canadian Office Action for Application No. CA 2487305 mailed Aug. 6, 2010.
Chinese Office Action for Application No. CN 03818027.8 mailed Jun. 9, 2006.
Chinese Office Action for Application No. CN 03818027.8 mailed Mar. 9, 2007.
Chinese Office Action for Application No. CN 03818027.8 mailed Aug. 20, 2007.
Chinese Office Action for Application No. CN 03818027.8 mailed Sep. 26, 2008.
Supplementary European Search Report for Application No. EP 03756329.3 mailed May 26, 2009.
Examination Report for for Application No. EP 03756329.3 mailed Apr. 6, 2010.
Examination Report for for Application No. EP 03756329.3 mailed Jul. 8, 2013.
Israeli Office Action for Application No. IL 165480 mailed Apr. 7, 2008.
Israeli Office Action for Application No. IL 165480 mailed May 6, 2009.
Japanese Office Action for Application No. JP 2004-508835 mailed Sep. 30, 2008.
Japanese Office Action for Application No. JP 2004-508835 mailed Feb. 16, 2010.
Japanese Office Action for Application No. JP 2004-508835 mailed Aug. 17, 2010.
International Search Report for PCT/US2003/017220 mailed Sep. 8, 2003.
International Preliminary Report on Patentability for Application No. PCT/US2003/017220 completed Feb. 22, 2004.
Office Action mailed Feb. 6, 2013 for U.S. Appl. No. 13/697,213.
Office Action mailed Mar. 25, 2013 for U.S. Appl. No. 13/697,213.

(56) References Cited

OTHER PUBLICATIONS

Office Action mailed Jul. 19, 2013 for U.S. Appl. No. 13/801,005.
Office Action mailed Jul. 19, 2013 for U.S. Appl. No. 13/801,075.
Office Action mailed Jul. 19, 2013 for U.S. Appl. No. 13/801,368.
Office Action mailed Jul. 1, 2013 for U.S. Appl. No. 13/801,429.
Office Action mailed Jul. 17, 2013 for U.S. Appl. No. 13/801,313.
Office Action mailed Jul. 19, 2013 for U.S. Appl. No. 13/801,373.
Office Action mailed Apr. 3, 2007 for U.S. Appl. No. 10/750,390.
Office Action mailed Aug. 28, 2007 for U.S. Appl. No. 10/750,390.
Office Action mailed Feb. 7, 2008 for U.S. Appl. No. 10/750,390.
Office Action mailed Aug. 20, 2008 for U.S. Appl. No. 10/750,390.
Appeal Brief mailed Jun. 23, 2009 for U.S. Appl. No. 10/750,390.
Appeal Brief mailed Jul. 21, 2009 for U.S. Appl. No. 10/750,390.
Supplemental Appeal Brief mailed Aug. 27, 2009 for U.S. Appl. No. 10/750,390.
Examiner's Answer to Appeal Brief mailed Nov. 10, 2009 for U.S. Appl. No. 10/750,390.
Reply Brief mailed Jan. 11, 2010 for U.S. Appl. No. 10/750,390.
Office Action mailed Sep. 7, 2011 for U.S. Appl. No. 10/750,390.
Office Action mailed May 10, 2012 for U.S. Appl. No. 10/750,390.
Appeal Brief mailed Dec. 11, 2012 for U.S. Appl. No. 10/750,390.
Office Action mailed Sep. 7, 2005 for U.S. Appl. No. 10/749,914.
Office Action mailed Apr. 17, 2006 for U.S. Appl. No. 10/749,914.
Office Action mailed Aug. 7, 2006 for U.S. Appl. No. 11/344,442.
Office Action mailed Mar. 6, 2007 for U.S. Appl. No. 11/344,442.
Office Action mailed Aug. 30, 2007 for U.S. Appl. No. 11/344,442.
Office Action mailed Feb. 7, 2008 for U.S. Appl. No. 11/344,442.
Appeal Brief mailed Jul. 3, 2008 for U.S. Appl. No. 11/344,442.
Examiner's Answer to Appeal Brief mailed Sep. 19, 2008 for U.S. Appl. No. 11/344,442.
Reply Brief and Appeal Brief mailed May 8, 2009 for U.S. Appl. No. 11/344,442.
Appeal Brief mailed May 20, 2009 for U.S. Appl. No. 11/344,442.
Miscellaneous Action with SSP mailed Jun. 4, 2010 for U.S. Appl. No. 11/344,442.
Office Action mailed Sep. 1, 2010 for U.S. Appl. No. 11/344,442.
Office Action mailed Feb. 27, 2008 for U.S. Appl. No. 11/506,137.
Office Action mailed Oct. 17, 2008 for U.S. Appl. No. 11/506,137.
Appeal Brief mailed Jul. 20, 2009 for U.S. Appl. No. 11/506,137.
Examiner's Answer to Appeal Brief mailed Nov. 3, 2009 for U.S. Appl. No. 11/506,137.
Reply Brief mailed Jan. 4, 2010 for U.S. Appl. No. 11/506,137.
Miscellaneous Action with SSP mailed Jun. 13, 2011 for U.S. Appl. No. 11/506,137.
Decision on Appeal mailed May 26, 2011 for U.S. Appl. No. 11/506,137.
Office Action mailed Jun. 4, 2013 for U.S. Appl. No. 11/506,137.
Office Action mailed Jul. 21, 2011 for U.S. Appl. No. 13/019,101.
Office Action mailed Feb. 13, 2012 for U.S. Appl. No. 13/019,101.
Office Action mailed Jun. 18, 2013 for U.S. Appl. No. 13/019,101.
Office Action mailed Aug. 11, 2005 for U.S. Appl. No. 10/448,632.
Office Action mailed Apr. 14, 2006 for U.S. Appl. No. 10/448,632.
Office Action mailed Nov. 1, 2006 for U.S. Appl. No. 10/448,632.
Appeal Brief mailed Mar. 30, 2007 for U.S. Appl. No. 10/448,632.
Office Action mailed Oct. 5, 2007 for U.S. Appl. No. 10/448,632.
Office Action mailed Jun. 17, 2008 for U.S. Appl. No. 10/448,632.
Office Action mailed Mar. 18, 2009 for U.S. Appl. No. 10/448,632.
Office Action mailed Nov. 4, 2009 for U.S. Appl. No. 10/448,632.
Appeal Brief mailed Sep. 6, 2010 for U.S. Appl. No. 10/448,632.
Examiner's Answer to Appeal Brief mailed Nov. 23, 2010 for U.S. Appl. No. 10/448,632.
Reply Brief mailed Jan. 24, 2011 for U.S. Appl. No. 10/448,632.
Decision on Appeal mailed Sep. 18, 2012 for U.S. Appl. No. 10/448,632.
Office Action mailed Apr. 16, 2013 for U.S. Appl. No. 10/448,632.
Office Action mailed Aug. 7, 2006 for U.S. Appl. No. 11/334,206.
Office Action mailed Mar. 6, 2007 for U.S. Appl. No. 11/334,206.
Office Action mailed Aug. 30, 2007 for U.S. Appl. No. 11/334,206.
Office Action mailed Jan. 24, 2008 for U.S. Appl. No. 11/334,206.
Appeal Brief mailed Jul. 14, 2008 for U.S. Appl. No. 11/334,206.
Examiner's Answer to Appeal Brief mailed Oct. 30, 2008 for U.S. Appl. No. 11/334,206.
Reply Brief mailed Dec. 30, 2008 for U.S. Appl. No. 11/334,206.
Reply Brief mailed May 8, 2009 for U.S. Appl. No. 11/334,206.
Miscellaneous Action with SSP mailed Jun. 4, 2010 for U.S. Appl. No. 11/334,206.
Office Action mailed Sep. 10, 2010 for U.S. Appl. No. 11/334,206.
Office Action mailed Apr. 19, 2011 for U.S. Appl. No. 11/334,206.
Office Action mailed Nov. 24, 2010 for U.S. Appl. No. 12/830,857.
Office Action mailed Jun. 10, 2011 for U.S. Appl. No. 12/830,857.
Office Action mailed Apr. 12, 2011 for U.S. Appl. No. 13/024,689.
Office Action mailed Jul. 21, 2011 for U.S. Appl. No. 13/024,689.
Office Action mailed Feb. 10, 2012 for U.S. Appl. No. 13/024,689.
Notice of Allowance mailed May 25, 2012 for U.S. Appl. No. 13/024,689.
Office Action mailed Nov. 4, 2010 for U.S. Appl. No. 12/796,213.
Office Action mailed Apr. 14, 2011 for U.S. Appl. No. 12/796,213.
[No Author Listed] About Soy Phospholipids. American Lecithin Company. Copyright 2000-2003. Last accessed online via http://www.americanlecithin.com/aboutphos.html on Sep. 29, 2007. 2 pages. (The year of publication is sufficiently earlier than the effective U.S. filed and any foreign priority date so that the particular month of publication is not in issue. See MPEP 609.04(a)).
[No Author Listed] Dow Corning MSDS Dow corning 200 fluid 5 cst. Material Safety Data Sheet. Version 1.3. Revision date Apr. 21, 2008. 8 pages.
[No Author Listed] Dow Corning Product Information: 200® Fluid Fluid 50cs, 100cs, 200cs, 350cs, 500cs, 1000cs. Ref. No. 25-991B-01. Dated Oct. 11, 2000. 4 pages.
[No Author Listed] Dow Corning. Information About Low Viscosity Silicone Fluids: 200® Fluid, 5cs; 200®Fluid, 10cs; 200® Fluid, 20cs. Product Information Sheet. Form No. 25-941-97. 1997. (The year of publication is sufficiently earlier than the effective U.S. filing date and any foreign priority date so that the particular month of publication is not in issue. See MPEP 609.04(a)) 2 pages.
[No Author Listed] Dow Corning® 190 Fluid Product Data Sheet. Dow Corning 190 Fluid is a silicone glycol coploymer. Last accessed on Sep. 18, 2006 <https://www.dowcorning.com/applications/search/default.aspx?R=66EN> 1 page.
[No Author Listed] Dow Corning® 190 Fluid. INCI Name: PEG/PPG-18/18 Dimethicone. Production Information Sheet. Ref No. 22-1616C-01. Dated May 17, 2002. 4 pages.
[No Author Listed] Dow Corning® 190 Fluid. Material Safety Data Sheet. Version 1.6. Revision date Sep. 19, 2005. 7 pages.
[No Author Listed] Frequently Asked Questions: How long can I store liposomes? Avanti Polar Lipids, Inc. Last accessed on Jun. 13, 2007. <http://avantilipids.com/DisplayFAQ.asp?Q=3> 1 page.
[No Author Listed] Frequently Asked Questions: How should I store my liposomes? Avanti Polar Lipids, Inc. Last accessed on Jun. 13, 2007. <http://avantilipids.com/DisplayFAQ.asp?Q=1> 1 page.
[No Author Listed] Frequently Asked Questions: What are the differences between liposomes and micelles? Avanti Polar Lipids, Inc. Last accessed on Jun. 13, 2007. <http://avantilipids.com/DisplayFAQ.asp?Q=4> 1 page.
[No Author Listed] Frequently Asked Questions: What is an SUV and LUV and how do they differ? Avanti Polar Lipids, Inc. Last accessed on Jun. 13, 2007. <http://avantilipids.com/DisplayFAQ.asp?Q=22> 1 page.
[No Author Listed] Google Search Results for "polyenylphosphatidylcholine phosphatidylcholi". Searched Sep. 29, 2007. 2 pages.
[No Author Listed] Liposome. Wikipedia. Last accessed on Jun. 11, 2007. <http://en.wikipedia.org/wiki/Liposome> 3 pages.
[No Author Listed] Liquid Crystal. Wikipedia. Last accessed on Jun. 22, 2009. <http://en.wikipedia.org/wiki/Liquid_crystal> 13 pages.
[No Author Listed] Oxytocin. Wikipedia. Last accessed on May 4, 2011. <http://en.wikipedia.org/wiki/Oxytocin> 16 pages.
[No Author Listed] Phosal® 50 PG data sheet. Sep. 10, 2007; 1 page.
[No Author Listed] Phosphatidylcholine. (Monograph). Alternative Medicine Review. Apr. 1, 2002. last accessed online via http://www.encyclopedia.com/doc/1G1-85522987.html on Sep. 29, 2007. 9 pages.

(56) References Cited

OTHER PUBLICATIONS

[No Author Listed] Preparations of liposomes. Avanti Polar Lipids, Inc. Last accessed on Jun. 13, 2007. <http://www.avantilipids.com/PreparationOfLiposomes.html> 3 pages.

[No Author Listed] Vasopressin. Wikipedia. Last accessed on May 4, 2011. <http://en.wikipedia.org/wiki/Vasopressin> 11 pages.

[No Author Listed], Poloxamer 407. Wikipedia Definition. Last Accessed on Feb. 1, 2013 from http://en.wikipedia.org/wiki/Poloxamer_407.

Abramson. Nitric oxide in inflammation and pain associated with osteoarthritis. Arthritis Res Ther. 2008;10 Suppl 2:S2. Epub Oct. 17, 2008. Review.

Ahn et al., Phase properties of liquid-crystalline Phosphatidylcholine/Phosphatidylethanolamine bilayers revealed by fluorescent probes. Arch Biochem Biophys. Sep. 15, 1999;369(2):288-94.

Bergenstahl et al., Phase equilibria in the system soybean lecithin/water. Progress in Colloid & Polymer Science. 1983;68:48-52. (The year of publication is sufficiently earlier than the effective U.S. filing date and any foreign date so that the particular month of publication is not in issue. See MPEP 609.04(a)).

Board Decision filed May 26, 2011 in co-pending U.S. Appl. No. 11/506,137.

Brandl et al., Morphology of semisolid aqueous phosphatidylcholine dispersions, a freeze fracture electron microscopy study. Chemistry and Physics of Lipids. May 30, 1997;87(1):65-72.

Cevc et al. "Ultraflexible Vesicles, Transfersomes, Have an Extremely Low Pore Penetration Resistance and Transport Therapeutic Amounts of Insulin Across the Intact Mammalian Skin." Biochem. et Biophys. Acta 1998, 1368, 201-215.

Cole et al., Challenges and opportunities in the encapsulation of liquid and semi-solid formulations into capsules for oral administration. Adv Drug Deliv Rev. Mar. 17, 2008;60(6):747-56. Epub Nov. 9, 2007.

Corswant et al., Triglyceride-based microemulsion for intravenous administration of sparingly soluble substances. J Pharm Sci. Feb. 1998;87(2):200-8.

Dermis [online] retrieved Jun. 21, 2013 from: en.wikipedia.org/wiki/Dermis. Wikipedia. 3 pages.

Engels et al., Liquid crystalline surfactant phases in chemical applications. J Mater Chem. 1998;8(6):1313-20. (The year of publication is sufficiently earlier than the effective U.S. filed and any foreign priority date so that the particular month of publication is not in issue. See MPEP 609.04(a)).

Esposito, Elisabette et al., "Lipid-Based Supramolecular Systems for Topical Application: A Preformulatory Study," Published(Italy) Nov. 18, 2003, 15 pages. AAPS PharmSci 2003; 5 (4) Article 30 (http://aapspharmsci.org).

Gad, Pharmaceutical Manufacturing Handbook: Production and Processes. John Wiley & Sons, Inc. New Jersey. 2008:1344.

Guo et al, "Transdermal Delivery of Insulin in Mice by Using Lecithin Vesicles as a Carrier," Drug Delivery, 7:113-116 (2000).

Huang et al., Nitric oxide-loaded echogenic liposomes for nitric oxide delivery and inhibition of intimal hyperplasia. J Am Coll Cardiol. Aug. 11, 2009;54(7):652-9.

Human Mouth [online] retrieved Jun. 21, 2013 from: en.wikipedia.org/wiki/Human_mouth. Wikipedia. 4 pages.

Imbert et al., Measuring the encapslation of cosmetic ingredients into liposomes: A method for large, hydrophilic compounds. J Soc Cosmet Chem. Nov./Dec. 1996;47(6):337-49.

Kirsten et al., Polyenylphosphatidycholine improves the lipoprotein profile in diabetic patients. International Journal of Clinical Pharmacology and Therapeutics. 1994;32(2):53-6. (The year of publication is sufficiently earlier than the effective U.S. filing date and any foreign date so that the particular month of publication is not issue. See MPEP 609.04(a)).

Lawrence et al., Microemulsion-based media as novel drug delivery systems. Adv Drug Deliv Rev. Dec. 6, 2000;45(1):89-121.

Lecithin the Multipurpose Emulsicier for Foods; [online] retrieved on Apr. 15, 2013 from: http://bluecoat-02/?cfru=aHR0cDovL3d3 dy5sZWNpdGluYS5pdC9wZGYvTGVjaXRoaW4IMjBUaGUIMj BNdwx0aXB1cnBvc2UIMjBlbXVsc21maWVyLnBkZg==; 8 pages.

Maeda et al., Preparation of poly(L-lactic acid)-polysiloxane-calcium carbonate hybrid membranes for guided bone regeneration. Biomaterials. Mar. 2006;27(8):1216-22. Epub Sep. 6, 2005.

Maurer et al., Developments in liposomal drug delivery systems. Expert Opin Biol Ther. 2001;1(6):1-25.

Miller et al., Recent developments in nitric oxide donor drugs. Br J Pharmacol. Jun. 2007;151(3):305-21. Epub Apr. 2, 2007.

Moller et al., Direct measurement of nitric oxide and oxygen partitioning into liposomes and low density lipoprotein. J Biol Chem. Mar. 11, 2005;280(10):8850-4. Epub Jan. 4, 2005.

Mueller-Goymann, Liquid crystals in drug delivery. Encylcopedia of Pharmaceutical Technology. 1988-2000;20:117-46. (The year of publication is sufficiently earlier than the effective U.S. filed and any foreign priority date so that the particular month of publication is not in issue. See MPEP 609.04(a)).

O'Donnell et al., Nitration of unsaturated fatty acids by nitric oxide-derived reactive species. Methods Enzymol. 1999;301:454-70.

Prescott, Methods in Cell Biology. Academic Press. 1976. Chapter 4. p. 34, 4 pages.

Qi et al., Interactions of insulin with dipalmitoylphosphatidylcholine liposomes. Acta Pharma Sinica. Dec. 2000;35(12):924-8. Chinese.

Rawat et al., Lipid carriers: a versatile delivery vehicle for proteins and peptides. Yakugaku Zasshi. Feb. 2008;128(2):269-80.

Seabra et al., Topically applied S-nitrosothiol-containing hydrogels as experimental and pharmacological nitric oxide donors in human skin. Br J Dermatol. Nov. 2004;151(5):977-83.

Shah et al., Cubic phase gels as drug delivery systems. Adv Drug Deliv Rev. Apr. 25, 2001;47(2-3):229-50.

Subczynski et al., Permeability of nitric oxide through lipid bilayer membranes. Free Radic Res. May 1996;24(5):343-9.

Troxerutin. Last accessed Jun. 12, 2008. <http://chamicalland21.com/lifescience/uh/TROXERUTIN.htm> 2 pages.

Tyle, Liquid crystals and their applications in drug delivery. Controlled Release of Drugs: Polymers and Aggregate Systems. Chapter 4. Morton Rosoff Ed., VCH Publishers New York, NY. 1989, pp. 125-162.

Valenta et al., Evaluation of novel soya-lecithin formulations for dermal use containing ketoprofen as a model drug. J Control Release. Jan. 3, 2000;63(1-2):165-73.

Van Beek et al., Thyroid hormones directly alter human hair follicle functions: anagen prolongation and stimulation of both hair matrix keratinocyte proliferation and hair pigmentation. J Clin Endocrinol Metab. Nov. 2008;93(11):4381-8. Epub Aug. 26, 2008.

Wimalawansa, Nitric oxide: novel therapy for osteoporosis. Expert Opin Pharmacother. Dec. 2008;9(17):3025-44. Review. Erratum in: Expert Opin Pharmacother. Apr. 1, 2010;11(6):1043.

Yuen et al., Treatment of chronic painful diabetic neuropathy with isosorbide dinitrate spray: a double-blind placebo-controlled crossover study. Diabetes Care. Oct. 2002;25(10):1699-703.

European Examination Report dated Jun. 25, 2014 for Application No. EP 03756329.3.

Office Action mailed Jan. 3, 2014 for U.S. Appl. No. 11/506,137.

Final Office Action mailed Aug. 21, 2014 for U.S. Appl. No. 11/506,137.

Advisory Action mailed Oct. 16, 2014 for U.S. Appl. No. 11/506,137.

Advisory Action mailed Dec. 11, 2013 for U.S. Appl. No. 13/019,101.

Office Action mailed Jan. 27, 2014 for U.S. Appl. No. 13/019,101.

Final Office Action mailed Aug. 20, 2014 for U.S. Appl. No. 13/019,101.

Advisory Action mailed Oct. 16, 2014 for U.S. Appl. No. 13/019,101.

Office Action mailed Dec. 22, 2014 for U.S. Appl. No. 13/947,353.

Office Action mailed Dec. 5, 2013 for U.S. Appl. No. 13/926,688.

[No Author Listed] Dow Corning® 190 Fluid. Textile, Leather & Non-woven. Silicone-ethylene oxide/propylene oxide copolymer. 3 pages. Mar. 3, 2005.

[No Author Listed] Phosal 50 PG; [online] retrieved on Nov. 26, 2013 from: http://www.lipoid.com/en/search/node/phosphatidylcholine?openedprd=true&lastedit=filter_a&filter_a=pharmaoral&showproduct=2157; 1 page.

(56) References Cited

OTHER PUBLICATIONS

[No Author Listed] Phospholipon® 80. Technical Data. American Lecithin Company. Copyright 2001-2011.
Duong et al. Intracellular nitric oxide delivery from stable NO-polymeric nanoparticle carriers. Chem Commun. 2013; 49:4190-4192.
Eccleston, Multiple-phase oil-in-water emulsions. J Soc Cosmet Chem. Jan./Feb. 1990;41:1-22.
Handa, Speaking of: Skin Care. Sterling Publishers. Aug. 1, 1998;51-2.
Hasenhuettl, Synthesis and commercial preperation of food emulsifiers. Food Emulsifiers and Their Applications. Chapter 2. 2008:11-37.
Liu et al. Soybean Phospholipids, Recent Trends for Enahncing the Diversity and Quality of Soybean Products; Prof. Dora Krezhova (Ed.); 2011. Available from: http://www.intechopen.com/books/recent-trends=for-enhancing-the-diversity-and-quality-of-soybean-products/soybean-phosphol.
Rydhag et al., the function of phospholipids of soybean lecithin in emulsions. JAOCS. Aug. 1981:830-7.
Shahidi, Nutraceutical and Specialty Lipids and their Co-Products. CRC Press. Mar. 14, 2006:515.

METHODS OF DELIVERING STABLE TOPICAL DRUG COMPOSITIONS

CROSS REFERENCE TO RELATED APPLICATIONS

This application is a continuation of U.S. patent application Ser. No. 13/019,101, field Feb. 1, 2011, which is a continuation of U.S. patent application Ser. No. 11/344,442 filed Jan. 31, 2006, which is a divisional application of U.S. patent application Ser. No. 10/749,914 filed Dec. 31, 2003, now U.S. Pat. No. 7,182,956 issued Feb. 27, 2007, which claimed priority benefits under 35 U.S.C. §119(e) of U.S. Provisional Patent Application Ser. No. 60/437,279 filed Dec. 31, 2002. Said Ser. No. 13/019,101 is also a continuation-in-part of U.S. patent application Ser. No. 11/334,206 for "Topical Drug Delivery Using Phosphatidylcholine", filed Jan. 18, 2006, which is a divisional patent application of U.S. patent application Ser. No. 10/448,632 for "Topical Drug Delivery Using Phosphatidylcholine," filed May 30, 2003, which claims priority benefits under 35 U.S.C. §119(e) of U.S. Provisional Patent Application Ser. No. 60/384,597 filed May 31, 2002. In addition, said Ser. No. 10/749,914 is a continuation-in-part of said Ser. No. 10/448,632.

FIELD OF THE INVENTION

The present invention relates to topical drug delivery compositions and methods of transdermal drug delivery. More specifically, the present invention relates to stable drug delivery compositions for topical administration.

BACKGROUND OF THE INVENTION

Topical drug delivery systems are known. These systems deliver drugs, therapeutic agents and other desired substances transdermally and may be designed to act locally at the point of application or to act systemically once entering the body's blood circulation. In these systems, delivery may be achieved by means such as direct topical application of a substance or drug in the form of an ointment or the like, or by adhesion of a patch with a reservoir or the like that holds the drug and releases it to the skin in a time-controlled fashion.

Transdermal delivery systems for agents such as drugs, pain relieving compounds, vitamins, and skin improving compounds have been in use for a number of years. These transdermal delivery systems using creams have been developed for use with analgesics and skin refining compounds. Transdermal systems using a patch have been developed for nicotine and estrogen therapies, for instance, estradiol technology described in U.S. Pat. No. 6,521,250 to Meconi, et al.

While effective for their purpose, these systems have typically only been useful for transdermal delivery of relatively small molecules. The skin's porous structure permits such small molecules to pass from the epidermis to the dermis via diffusion. However, large molecules, such as insulin, are not able to diffuse through the skin and cannot be delivered by these known means. One such solution has been provided in U.S. patent application Ser. No. 10/448,632 to Perricone, the disclosure of which is incorporated herein by reference.

While the delivery of large molecules such as insulin have been addressed, such systems do not address the storage and retention of the effectiveness of the drug to be delivered. Many pharmaceuticals and biologically active compounds, such as insulin, must be kept cool and away from heat to remain effective and prevent denaturing at ambient temperatures. Such substances may not be stored or carried (without refrigeration) by the user. Often drugs like insulin must be administered throughout the day and should be in ready-access to or carried by the user, which may expose the compound to high temperatures. As such, there remains a need to stabilize compositions, including insulin, so that they are resistant to warmer temperatures and have a longer life at these temperatures without a need for refrigeration

SUMMARY OF THE INVENTION

A composition for transdermal delivery of a macromolecule comprises a phosphatidylcholine carrier component entrapping the macromolecule, wherein the carrier component stabilizes the macromolecule at room temperature.

A method for administering a drug or other active agent comprises applying to skin composition containing an effective amount of the drug or active agent, a carrier having a phosphatidylcholine component entrapping the drug or active agent.

DETAILED DESCRIPTION OF THE INVENTION

Phosphatidylcholine is used as a carrier for the topical delivery of polypeptides and macromolecules in the practice of this invention. Phosphatidylcholine is a basic component of cell membrane bilayers and the main phospholipid circulating in the plasma. Phosphatidylcholine is highly absorbable and supplies choline which is needed to facilitate movement of fats and oils across and maintain cell membranes in animals.

Topical delivery compositions of the present invention are non-polar and formulated to contain polypeptides and macromolecules soluble in phosphatidylcholine, which are then applied to skin for transdermal delivery of the macromolecule. Topical delivery compositions of the invention are efficacious in the delivery of macromolecular drugs that are conventionally administered intramuscularly, intravenously or orally, including, but not limited to polypeptides such as insulin and somatropin, prostaglandins, glucocorticoids, estrogens, androgens, and the like.

It is an advantage of the invention that topical administration of a composition and transdermal delivery of the drug or active agent therein is easier and pleasanter as an administration route than injections, particularly for drugs such as insulin that must be given to patients over a period of time, or for a lifetime. Furthermore, unlike oral administration where a substantial amount of the drug can be destroyed in the digestive process, the drugs in a topical application are not wasted. Topical application allows a steady diffusion of the drug to the desired target area without the cyclic dosages typical of orally or parenterally administered drugs.

The term "phosphatidylcholine" as used herein means a mixture of stearic, palmitic, and oleic acid diglycerides linked to the choline ester of phosphoric acid, commonly called lecithin. Many commercial lecithin products are available, such as, for example, those sold under the tradenames Lecithol®, Vitellin®, Kelecin®, and Granulestin® because lecithin is widely used in the food industry. Compositions of the invention can contain synthetic or natural lecithin, or mixtures thereof. Natural preparations are preferred because they exhibit desirable physical characteristics and are both economical and nontoxic.

Preferred topical delivery compositions of the present invention additionally contain polyenylphosphatidylcholine (herein abbreviated "PPC") to enhance epidermal penetration. The term "polyenylphosphatidylcholine" as used herein means any phosphatidylcholine bearing two fatty acid substituents, wherein at least one is an unsaturated fatty acid with at least two double bonds such as linoleic acid. Certain types of soybean lecithin and soybean fractions, for example, contain higher levels of polyenylphosphatidylcholine, with dilinoleoylphosphatidylcholine (18:2-18:2 phosphatidylcholine) as the most abundant phosphatidylcholine species, than conventional food grade lecithin, and are useful in formulating topical delivery compositions of the invention. Alternatively, conventional soybean lecithin is enriched with polyenylphosphatidylcholine by adding soybean extracts containing high levels of polyenylphosphatidylcholine. As used herein, this type of phosphatidylcholine is called "polyenylphosphatidyl-choline-enriched" phosphatidylcholine (hereinafter referred to as PPC-enriched phosphatidylcholine), even where the term encompasses lecithin obtained from natural sources exhibiting polyenylphosphatidylcholine levels higher than ordinary soybean varieties. These products are commercially available from American Lecithin Company, Rhône-Poulenc and other lecithin vendors. American Lecithin Company markets its products with a "U" designation, indicating high levels of unsaturation; Rhône-Poulenc's product is a soybean extract containing about 42% dilinoleoylphosphatidylcholine and about 24% palmitoyllinoleylphosphatidylcholine (16:0-18:2 PC) as the major phosphatidylcholine components.

While not wishing to be bound to any theory, it is believed that the PPC-enriched phosphatidylcholine forms a bilayer enveloping the polypeptide or macromolecule to create the topical drug delivery composition, contributing to the stability of the active molecule and enhancing penetration. Further, the topical drug delivery composition may be in liquid crystal phase, with the PPC-enriched phosphatidylcholine loosely arranged in multilamellar fashion, with the polypeptide or macromolecule being bonded and entrapped within the lipid bilayers formed therein, as disclosed in U.S. patent application Ser. No. 10/448,632 to Perricone. This forms a loosely arranged, yet stable, PPC-enriched phosphatidylcholine-drug complex that further increases penetration and delivery of the polypeptide or macromolecule to the dermal vasculature.

The disclosure of U.S. patent application Ser. No. 11/334,206 for "Topical Drug Delivery Using Phasphatidylcholine", filed Jan. 18, 2006 is hereby incorporated by reference.

Topical drug delivery compositions of the present invention provide an administration route that is a marked improvement over conventional insulin injections, considerably easier and pleasanter. It is a further advantage that compositions of the invention are also stable at room temperature, providing considerable convenience for insulin users who, in the past, have had to deal with the refrigerated insulin products commercially available. Also, insulin compositions according to the present invention have longer shelf lives (whether stored at room temperature or refrigerated) and will not denature at room temperature as would traditional insulin treatments.

Insulin useful in the topical drug delivery compositions of the present invention is commercially available from a variety of sources, marketed under the tradenames Humulin®, Novolin®, Humalog®, Inutral®, among others. Some of these products contain porcine sequences. Compositions of the invention are preferably formulated with recombinant human polypeptides such as those obtained from Sigma Co., Spectrum Chemicals and Laboratories, and similar vendors and employed in the examples that follow. It is an advantage of the invention that topical drug delivery compositions carrying insulin are formulated with commercially available ingredients.

Topical drug delivery compositions are generally formulated with a carrier comprising a PPC-enriched phosphatidylcholine material with the trade name NAT 8729 (commercially available from vendors such as Rhône-Poulenc and American Lecithin Company) and at least one polyglycol (polyhydric alcohol of a monomeric glycol such as polyethylene glycol (PEG) having molecular weights of 200, 300, 400, 600, 1000, 1450, 3350, 4000, 6000, 8000 and 20000. Further, this carrier may comprise a surfactant such as a siloxylated polyether comprising dimethyl, methyl(propylpolyethylene oxide propylene oxide, acetate) siloxane or silicone glycol copolymer fluid commercially available from vendors such as Dow Corning, e.g. poly(oxyehtylene.oxypropylene) methyl polysiloxanne copolymer sold under the tradename Dow Corning 190 surfactant, and lubricant such as silicone fluids containing low viscosity polydimethylsiloxane polymers, methylparaben (p-hydroxy benzoic acid methyl ester) commercially available from vendors such as Down Corning (under the tradename Dow Corning 200 silicone fluid). Additionally, purified water may be added to the carrier. The carrier is then mixed with a preparation of the particular polypeptide(s) or macromolecule(s) in an amount to obtain the desired strength in the final composition. The following examples are presented to further illustrate and explain the present invention and should not be taken as limiting in any regard.

Preparation of Stable Insulin Compositions

Example 1

Stable insulin topical preparations were formulated by first preparing a base solution. A polyenylphosphatidylcholine material denoted NAT 8729 which contained 80.6% PPC-enriched phosphatidylcholine and 4.9% lysophosphatidylcholine was obtained from Rhône-Poulenc. NAT 8729 (45% w/w) was shaved and added to a mixture of polyglycol E200 (50% w/w) and polyglycol E400 (5% w/w) both obtained from Dow Corning. The base solution was then covered well and lightning mixed with a special disintegration head impeller slowly at 800 rpm with slight heat. The temperature did not go above 40° C. Typical mixing times were 5 hours. The final solution is a crystal clear, viscous amber solution with no sediments or separations.

Into this base solution (97.25% w/w) was then mixed a Dow Corning Fluid 190 (1.00% w/w) [a siloxylated polyether comprising dimethyl, methyl(propylpolyethylene oxide propylene oxide, acetate) siloxane]; a Dow Corning silicone fluid denoted 200-5 or 10cst (1.00% w/w) [silicone fluids containing low viscosity polydimethylsiloxane polymers]; and methylparaben [p-hydroxy benzoic acid methyl ester] obtained from vendor Mallinckrodt (0.75% w/w). The ingredients were homogenized with 3850 rpm with a 0.45 micron screen as follows. The methylparaben was first added to the base solution and mixed for at least an hour until a complete solution formed. Then the Dow Corning 200-5 or 10cst was slowly added and mixed until a clear solution formed. Afterwards the Dow Corning Fluid 190 was added slowly and mixed into the solution to form the carrier.

Insulin preparations of the invention were then made using the carrier in two strengths: 50 units and 100 units, by simply dissolving RNA-derived recombinant human insulin obtained from Sigma into the carrier. It was readily soluble in the carrier.

In testing the stability of the stable insulin composition, insulin standards were prepared at 1 mg/ml in 0.01 N HCl using Sigma insulin. (One mg of this material exhibits an activity of 28 insulin units.) Stable insulin compositions samples were prepared at 1 mg/1 ml base by mixing at room temperature for 60 minutes. This mixture was then divided in half, half of which was stored at 4° C., and the other half stored at room temperature. Separation analyses, High Performance Liquid Chromatography (RP-HPLC) and High Performance Capillary Electrophoresis (HPCE), of insulin standards and insulin compositions of the invention which were stored at different temperatures for different periods of time were performed.

The RP-HPLC and HPCE analyses indicated that insulin standards that were stored at 4° C. or −20° C. were stable after 65 days, but insulin standards stored at room temperature started to denature within 7 days. The RP-HPLC and HPCE profiles of insulin compositions of the invention, on the other hand, were stable at both room temperature and at 4° C., and did not change after 65 days. The results clearly showed that the carrier prevented the denaturing of the insulin stored at room temperature.

Preparation of Stable Insulin Compositions

Example 2

Stable insulin compositions were formulated by first preparing a base solution. Polyglycol E200 (PEG-200) (50% w/w) was weighed and polyglycol E400 (PEG-400) (5% w/w) was added to the same container to obtain the desired weight, (both obtained from Dow Corning). PEG-200 and PEG-400 were lightning mixed at 3840° C. with IKA model RW20 using a disintegration head impeller slowly at 800 rpm (speed 1), yielding PEG-200/PEG-400 solution. A PPC-enriched phosphatidylcholine material denoted NAT 8729 containing 80.6% PPC-enriched phosphatidylcholine and 4.9% lysophosphatidylcholine was obtained from Rhône-Poulenc. NAT 8729 (45% w/w) was shaved and added to PEG-200/PEG-400 solution, covered and mixed, with temperature not exceeding 40° C., until a clear, viscous amber solution with no sediments or separations resulted. The mixing time was approximately five hours. An alternative mixture can be prepared by covering and mixing the solution overnight without heat for a 95-96% yield. The solution was removed from heat and transferred to Ross Homogenizer (Model HSM100LC) using smallest mesh screen.

A Dow Corning Fluid was then prepared. Dow Corning Fluid denominated 190 (1.00% w/w) [a siloxylated polyether comprising dimethyl, methyl(propylpolyethylene oxide propylene oxide, acetate) siloxane] and Dow Corning Fluid denoted 200-5 or 10 cst (1.00% w/w) [silicone fluids containing low viscosity polydimethylsiloxane polymers] were mixed together in a container with a clean spatula.

The solution (53.25% w/w) was warmed to 40° C. and mixed at 800 rpm. Typical mixing times were approximately 5 hours. The solution was then milled at 3800 rpm and the Dow Corning Fluid mixture was added very slowly until a clear solution resulted. Methyl Paraben (p-hydroxy benzoic acid methyl ester) obtained from Mallinckrodt (0.75% w/w) was added at once and mixed until a complete solution resulted. Purified water warmed to 40° C. was added very slowly to solution while milling at 7500 rpm for about three minutes. At end of milling, speed was increased to 10,000 rpm for few seconds before stopping. The solution was removed and swept with paddle head using IKA Model RW-20 until cooled to room temperature. This step is very critical and if it is not done properly it will generate a biphasic end product. The general rule is to use a container having a volume twice that of the solution so the homogenizer head is well embedded in the solution. The solution was then cooled to room temperature.

USP human recombinant insulin in obtained from Spectrum Chemicals and Laboratories (Product #11247) was prepared in 0.01 N HCl at 50 mg/ml, and gently, yet well mixed. This insulin preparation was then added very slowly to the above solution to obtain a final concentration of 500 units/ml or 20 mg/ml. Mixing was continued at room temperature for at least one hour. The final stable insulin composition was stored at 4° C. in amber air-tight container.

RP-HPLC and HPCE analyses of insulin standards (prepared at 5 mg/ml in 0.01 N HCl) and stable insulin compositions of the invention which were stored at different temperatures for different periods of time were performed. The results indicated that standard insulin standards stored at 4° were stable up to 22 weeks and started to denature after 34 weeks, whereas when stored at room temperature started to denature within only 1 week. However, the stable insulin compositions prepared in accordance with the above disclosures that were stored at room temperature were stable up to at least 22 weeks, which is 21 weeks longer than the standard. The results showed no change in shelf-life from the standard for stable insulin compositions stored at 4° C. (no change after 34 weeks).

Stable topical drug delivery compositions of the present invention may be employed to deliver and stabilize polypeptides transdermally, including but not limited to insulin, oxytocin, vasopressin, insulin, somatotropin, calcitonin, chorionic gonadotropin, menotropins, follitropins, somatostatins, progestins, and combinations of any of these. These drugs are readily available from a variety of commercial sources. Somatotropin (pituitary growth hormone) is marketed under the tradenames Gentropin®, Humatrope®, Nutropin®, and Serostim®.

A drug delivery composition formulated with somatotropin was formulated in one trial with 85% phosphatidylcholine to which lipoic acid and ascorbyl palmitate were added. Somatotropin readily dispersed in phosphatidylcholine and remained stable in it. Growth hormone appeared to penetrate the skin well when the composition was topically applied.

The present invention may also be used to provide topical delivery of active agents other that drugs, for example, skin care agents. The invention is particularly useful with large molecules that are used in some cosmetic formulations, including peptides and polymers.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention.

What is claimed is:

1. A carrier composition for transdermal delivery of insulin, comprising a siloxylated polyether comprising dimethyl, methyl(propylpolyethylene oxide propylene oxide, acetate) siloxane, at least one polyglycol, a silicone fluid comprising polydimethylsiloxane, and polyenylphosphatidylcholine, the carrier composition comprising the insulin for transdermal delivery to dermal vasculature, wherein the polyenylphosphatidylcholine stabilizes the insulin such that the insulin is stable when stored at room temperature for at least 65 days.

2. The composition of claim 1, wherein the at least one polyglycol comprises polyglycol having a molecular weight of 200 and polyglycol having a molecular weight of 400.

3. The composition of claim 1, wherein the carrier composition further comprises methyl paraben.

4. A stable topical insulin composition, comprising:
a carrier comprising a siloxylated polyether, at least one polyglycol, a silicone fluid, and polyenylphosphatidylcholine; and
insulin comprised within the carrier for transdermal delivery of the insulin to dermal vasculature, wherein the polyenylphosphatidylcholine stabilizes the insulin such that the insulin is stable when stored at room temperature for at least 65 days.

5. The composition of claim 4, wherein the siloxylated polyether comprises dimethyl, methyl(propylpolyethylene oxide propylene oxide, acetate) siloxane.

6. The composition of claim 4, wherein the at least one polyglycol comprises polyglycol having a molecular weight of 200 and polyglycol having a molecular weight of 400.

7. The composition of claim 4, wherein the silicone fluid comprises polydimethylsiloxane.

8. The composition of claim 4, wherein the carrier further comprises methyl paraben.

\* \* \* \* \*

UNITED STATES PATENT AND TRADEMARK OFFICE
CERTIFICATE OF CORRECTION

PATENT NO. : 9,060,925 B2
APPLICATION NO. : 13/947329
DATED : June 23, 2015
INVENTOR(S) : Nicholas V. Perricone et al.

Page 1 of 1

It is certified that error appears in the above-identified patent and that said Letters Patent is hereby corrected as shown below:

On the Title page, Item (60) should read:

(60)  Continuation of application No. 13/019,101, filed on Feb. 1, 2011, which is a continuation-in-part of application No. 11/334,206, filed on Jan. 18, 2006, now abandoned, which is a divisional of application No. 10/448,632, filed on May 30, 2003, said application No. 13/019,101 is a continuation of application No. 11/344,442, filed on Jan. 31, 2006, now abandoned, which is a division of application No. 10/749,914, filed on Dec. 31, 2003, now Pat. No. 7,182,956, which is a continuation-in-part of application No. 10/448,632, filed on May 30, 2003.

(60)  Provisional application No. 60/384,597, filed on May 31, 2002, provisional application No. 60/437,279, filed on Dec. 31, 2002.

Signed and Sealed this
Thirteenth Day of October, 2015

Michelle K. Lee
*Director of the United States Patent and Trademark Office*